US00PP17094P3

(12) United States Plant Patent
Kwantes

(10) Patent No.: US PP17,094 P3
(45) Date of Patent: Sep. 12, 2006

(54) ***SCABIOSA COLUMBARIA* PLANT NAMED 'PINK LEMONADE'**

(50) Latin Name: *Scabiosa columbaria*
Varietal Denomination: Pink Lemonade

(75) Inventor: Michael G. Kwantes, Allegan, MI (US)

(73) Assignee: Walters Gardens, Inc, Zeeland, MI (US)

( * ) Notice: Subject to any disclaimer, the term of this patent is extended or adjusted under 35 U.S.C. 154(b) by 26 days.

(21) Appl. No.: 11/039,110

(22) Filed: Jan. 19, 2005

(65) Prior Publication Data

US 2006/0162031 P1 Jul. 20, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

The new and distinctive plant of Pincushion Flower known as *Scabiosa columbaria* 'Pink Lemonade' and characterized by a golden margin on green leaves, with pink flowers and compact habit especially suitable for potted culture and landscape usage as either a specimen or in large masses.

2 Drawing Sheets

Botanical classification: *Scabiosa columbaria* in the family Asteraceae.
Variety denomination: 'Pink Lemonade'.

CROSS-REFERENCE TO RELATED APPLICATIONS

*Scabiosa caucasica* plant named 'Ultra Violet' U.S. Plant Pat. No. 14,038. *Scabiosa* plant named 'Walminiblue' U.S. Plant Pat. No. 13,446. *Scabiosa* plant named 'Walminipink' U.S. Plant Pat. No. 13,442. Scabious plant named Pink Mist U.S. Plant Pat. No. 8,957.

BACKGROUND OF THE INVENTION

The present invention relates to a new and distinct cultivar of *Scabiosa columbaria* plant named 'Pink Lemonade'. The plant was discovered as an uninduced whole plant mutation by Michael G. Kwantes during the summer of 2002 in a greenhouse-growth batch of *Scabiosa* 'Butterfly Blue' (not patented) at a wholesale perennial nursery in Zeeland, Mich., USA.

The plant has been asexually propagated by cuttings at the same wholesale perennial nursery in Zeeland, Mich., USA with the resulting plants maintaining the identical characteristics of the parent plant. The phenotype may vary with differences in the environment but without any deviation in the genotype. The plant has not been evaluated under all possible environmental conditions.

BRIEF SUMMARY OF THE INVENTION

*Scabiosa* 'Pink Lemonade' is unique from all other known varieties of *Scabiosa* in the following distinctions:

1. Small compact habit
2. Pinkish lavender flowers
3. Yellowish green variegated margin

*Scabiosa* 'Pink Lemonade' is the only variegated pincushion flower known to the discoverer. The plant can be compared to *Scabiosa* 'Blue Mist' from which it sported in that in addition to having a yellow to greenish-yellow margin the flower is more pink tinted and less blue tinted. The flower color is much closer to 'Pink Mist' which is also not variegated.

BRIEF DESCRIPTION OF THE DRAWINGS

The photographs of the new plant demonstrate the unique characteristics and overall appearance of the new cultivar 'Pink Lemonade'. The colors are as accurate as reasonably possible with color reproductions. Variations such as temperature, light source, light quality and direction may cause the appearance of different colors.

DETAILED BOTANICAL DESCRIPTION

Figure 1:
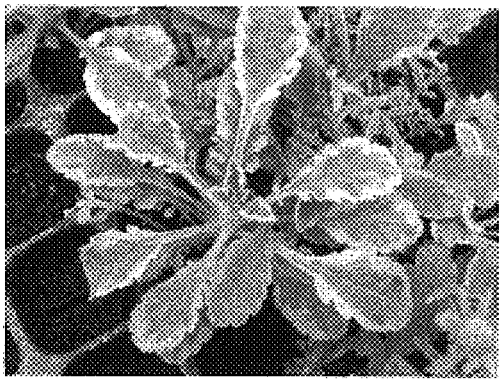
FIG. 1—Shows a young plant with less dissected foliage and bright variegation FIG. 2—Shows a close-up of a flower.
Figure 2:
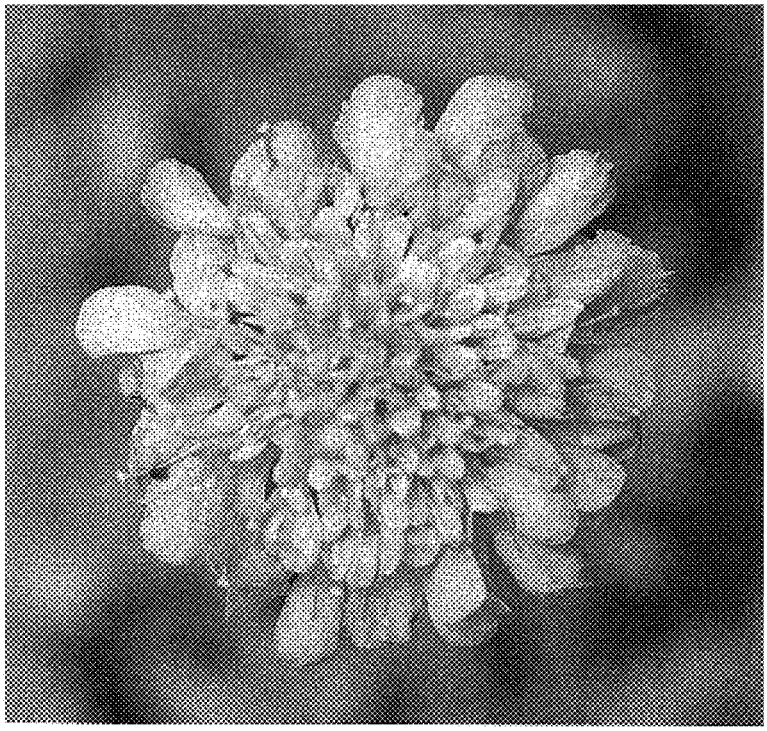
Figure 3:
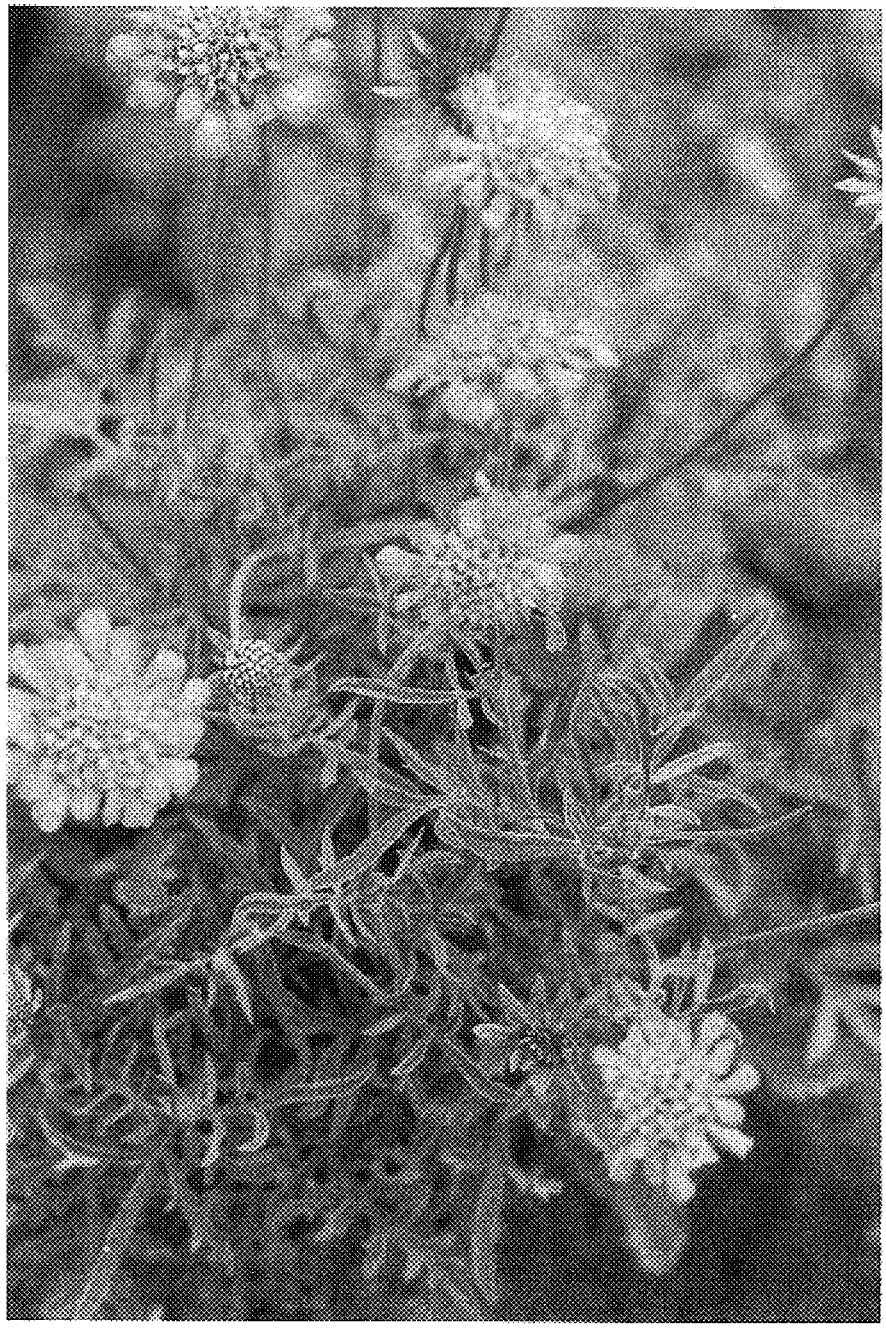
FIG. 3—Shows a mature plant in flower with finely dissected foliage.

The plant being described is a two-year old plant grown in silty-sand trial garden at a wholesale perennial nursery in Zeeland, Mich. USA. Plant gets full sun exposure with supplemental fertilizer and water.

Habit: Low-branched, deciduous, herbaceous perennial with variegated foliage in a rosette 15 to 20 cm tall and 25 to 30 cm wide; flowers on branched peduncle up to 30 cm tall and combined to a width of 35 cm; fibrous rooted;

Leaves: Leaf overall is 12 to 18 cm long; blade 8 to 12 cm long by 4 to 6 cm wide at the widest part; crenate at apex, pinnatifidly parted at base of blade; less dissected earlier in season and as young plant; lightly pubescent on top and bottom; margin of the L II tissue 1 to 5 mm wide, with an occasional unconnected, toothed L I margin layer outside of the L II about 1 mm wide and 1 to 1.5 mm long, L III or leaf center is 2.5 mm to 5 mm wide;

*Color in summer.*—Ventral L I toothed margin RHS 137A, L II RHS 144 B, and center L III is between RHS 139 A and RHS 137 A; dorsal L I layer RHS 137B in occasional spots of 1 mm or less in each direction, not necessarily directly below the green L I tissue of the ventral margin; L II RHS 144A; L III RHS 137B;

*Color in spring.*—Ventral L III closest to RHS 137 B, L II is RHS 144 B, and L I is RHS 137 A; dorsal side L III is 138 B, L II is between RHS 144 A and RHS 144 B, and L I is RHS 137 C.

Veins: Netted, RHS 138B center part of the leaf and near apex on dorsal side, midrib lightening to RHS 138D near stem; outer veins same color as surrounding tissue in the leaf center and margin on ventral surface; ventral side of the midrib is about 2 mm wide surface, lighter than RHS 138D closer to stem, RHS 139A to RHS 137A near middle apex of leaf;

Petioles: 3 to 6 cm long, 1.5 mm wide at stem flaring to 3 mm wide at leaf blade, RHS 144 B and RHS 138 D on ventral edges and center respectively; RHS 144 A and RHS 138D on ventral edge and center respectively;

Sepals: 8 to 18; size up to 10 mm long and 3 mm wide; color RHS 139C ventral side, RHS 138 B with a fine stripe less than 1 mm wide in the center of RHS 139 A on the dorsal side;

Flowering habit: Compound heads, aggregate of achene; single or branched low on the stem; color is more similar to 'Pink Mist' (not patented) than 'Butterfly Blue' (not patented);

Flower buds: About two days prior to opening RHS N57 D, 2 mm wide, 3 to 4 mm long.

Ray flowers: 15 to 24 per flower.

*Petals.*—Five, simple, entire, spatulate, fused at mid-point, single largest petal on outside of floret 12 to 15 mm long by 4 mm wide, side two petals at near right angles to outer petal 9 to 10 mm long by 3 to 4 mm wide, two smallest petals on inside of floret 5 to 6 mm long and 2 mm wide; ventral surface of longest three petals RHS N80 B toward apex, RHS 76 C near fused portion; ventral surface of shorter two petals between RHS N78 B and RHS N78 C at apex; dorsal apex of longest three petals RHS 77 C and closest to RHS 76 D near fused part; dorsal apex of shortest two petals RHS N78 B. Both dorsal and ventral sides of all petals are white at base.

*Gynoecium.*—One pistil, 10 mm long and less than 0.5 mm wide, at apex RHS 76 C, white at base;

*Androecium.*—Five, filaments fused to inner corolla surface, 2 mm long and less than 0.25 mm wide, white; anthers 1 mm long and less than 0.5 mm wide, RHS 161 C; pollen RHS 11 A;

Disc Flowers: 40 to 60 per head.

*Petals.*—Five, rounded apex, one petal about 1 mm longer than the others; 7 to 8 mm long, and fused except for last 1 mm; ventral side of longest petal RHS 77 B at apex, other petals ventral side apex is RHS 76A; dorsal side of longest petal is RHS 77 B at the apex; both sides of other petals at apex is between RHS 76 A and RHS 76 B; base of all petals is white.

*Gynoecium.*—One pistil, 10 mm long and less than 0.5 mm wide, RHS 76 C at apex, white at base;

*Androecium.*—Five, filaments fused to inner corolla surface, 1 mm long and less than 0.25 mm wide, white; anthers 1 mm long and less than 0.5 mm wide, RHS 161 C; pollen RHS 11 A;

Peduncle: 6 to 8 per plant; RHS 138 B; 10 to 20 cm tall and 5 mm thick at base; branching starting at 3 to 5 cm above soil; 22 to 36 flower heads per peduncle; up to 25 cm across;

Pedicel: Vary in length from 5 to 25 cm long, 3 mm wide; RHS 138 B;

Fragrance: Sweet hyacinth-like on mature flowers;

Seeds: 2 mm long, RHS N 199 C, viability unknown; 1 mm wide at distal end, triangular narrowing to a point at proximal end; with four to five 2 mm long thin bristles at distal end; bristles RHS N187 A;

Time to initiate roots: 10 to 21 days;

Growth rate: Moderate, finishing in a 7 cm pot from cuttings in 3 to 4 months.

The plant does not appear to be susceptible to many pests or diseases, but does not show any resistance beyond that common to the genus.

I claim:

1. The new and distinct Pincushion Flower plant, *Scabiosa columbaria* 'Pink Lemonade', with golden margins and compact habit, essentially as herein described and illustrated suitable as a landscape specimen, mass or potted culture.

* * * * *

SCABIOSA COLUMBARIA PLANT NAMED 'PINK LEMONADE'

SCABIOSA COLUMBARIA PLANT NAMED 'PINK LEMONADE'